US009756854B2

(12) United States Patent
Rodriguez-Kabana et al.

(10) Patent No.: US 9,756,854 B2
(45) Date of Patent: *Sep. 12, 2017

(54) TREATED BIODIESEL GLYCERIN

(71) Applicant: Auburn University, Auburn, AL (US)

(72) Inventors: Rodrigo Rodriguez-Kabana, Aubrun, AL (US); Robert H. Walker, Auburn, AL (US)

(73) Assignee: Auburn University, Auburn, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/271,550

(22) Filed: Sep. 21, 2016

(65) Prior Publication Data

US 2017/0006862 A1    Jan. 12, 2017

Related U.S. Application Data

(63) Continuation of application No. 14/886,374, filed on Oct. 19, 2015, now Pat. No. 9,451,766, which is a continuation of application No. 14/268,381, filed on May 2, 2014, now Pat. No. 9,181,139, which is a continuation of application No. 13/836,460, filed on Mar. 15, 2013, now Pat. No. 8,754,134, which is a continuation of application No. 12/040,484, filed on Feb. 29, 2008, now Pat. No. 8,519,009.

(60) Provisional application No. 60/937,243, filed on Jun. 26, 2007, provisional application No. 60/964,913, filed on Aug. 15, 2007, provisional application No. 60/904,672, filed on Mar. 2, 2007, provisional application No. 60/937,128, filed on Jun. 26, 2007.

(51) Int. Cl.
*A01N 31/02* (2006.01)
*C05G 3/02* (2006.01)
*C05C 9/00* (2006.01)

(52) U.S. Cl.
CPC .............. *A01N 31/02* (2013.01); *C05C 9/00* (2013.01); *C05G 3/02* (2013.01); *Y02E 50/343* (2013.01); *Y02W 30/47* (2015.05)

(58) Field of Classification Search
None
See application file for complete search history.

(56) References Cited

U.S. PATENT DOCUMENTS

| | | |
|---|---|---|
| 5,057,141 A | 10/1991 | Rodriquez-Kabana et al. |
| 5,084,477 A | 1/1992 | Walter et al. |
| 1,916,743 A | 7/1993 | Schwenk et al. |
| 5,288,488 A | 2/1994 | Backman et al. |
| 5,314,678 A | 5/1994 | Grummon et al. |
| 6,524,998 B1 | 2/2003 | Kloepper et al. |
| 6,720,352 B1 | 4/2004 | Rodriguez-Kabana |
| 7,462,579 B2 | 12/2008 | Rodriguez-Kabana et al. |
| 2006/0089263 A1 | 4/2006 | Rodriguez-Kabana |
| 2006/0276342 A1 | 12/2006 | Krahmer et al. |
| 2011/0044972 A1 | 2/2011 | Fieldhouse et al. |

FOREIGN PATENT DOCUMENTS

| | | |
|---|---|---|
| DE | 10344919 | 4/2005 |
| WO | 99/07221 | 2/1999 |

OTHER PUBLICATIONS

Ahn et al., "A Low-Waste Process for the Production of Biodiesel," Separation Science and Technology, 1995, 30 (7-9): 2021-2033.
Akhtar, et al., "Role of Organic Soil Amendment and Soil Organisms in the Biological Control of Plant-Parasitic Nematodes: A Review", Bioresource Technology, 2000, 74: 35-47.
Belcher, J.L., R.H. Walker, R. Rodriguez-Kabana, E. Geurtal, and L.E. Simmons. 2005. Tomato and Pest Response to Acrolein (2-Propenal). Proceedings Annual International Research Conference on Methyl Bromide Alternatives and Emissions Reductions. Oct. 31-Nov. 3, 2004. San Diego, California. Paper No. 24.
Belcher, J.L., R.H. Walker, R. Rodriguez-Kabana 2004. Acrolein and Propylene Oxide: Alternatives to Methyl Bromide for Weed Control in Turf. Proceedings Annual International Research Conference on Methyl Bromide Alternatives and Emissions Reductions. Oct. 31-Nov. 3, 2004. Orlando, Florida. Paper No. 23.
Bello et al., "Biofumigation and nematode control in the Mediterranean region", Nematology Monographs & Perspectives, 2004, 2:133-149.
Bournay et al., "New Heterogeneous Process for Biodiesel Production: A Way to Improve the Quality and the Value of the Crude Glycerin Produced by Biodiesel Plants," Catalysis Today, vol. 106, pp. 190-192, (2005).
Davies. W., "The Deterioration of Fats and the Development of Rancidity", Industrial Chemist and Chemical Manufacture, 1928, 4: 269-272.
Ishizaki et al., "Effects of Biodiesel Fuel Byproduct (Crude Glycerin) Addition to Composting of Dairy Cattle Excrement," Database Caplus Chemical Abstracts Service, XP002520961, 2007, 6: 45-54.
Merck Index. 1989. 11th Edition. Merck & Co., Inc. Rahwayt, J.J. USA.
Meister Pro. 2006. Crop Protection Handbook. Meister Media, Willoughby, OH.
Rodriguez-Kabana et al., "Biological control of nematodes: Soil amendments and microbial antagonists", Plant and Soil, 1987, 100:237-247.
Rodriguez-Kabana et al., "A Simple Incubation Method for the Extraction of Nematodes From Soil", Nematropica, 1981, 11: 175-186.
Rodriguez-Kabana, "Organic and Inorganic Nitrogen Amendments to Soil as Nematode Suppresants", Journal of Nematology, 1986: 129-135.

(Continued)

*Primary Examiner* — David J Blanchard
*Assistant Examiner* — Daniel F Coughlin
(74) *Attorney, Agent, or Firm* — Andrus Intellectual Property Law, LLP

(57) ABSTRACT

Disclosed are compositions that include treated biodiesel glycerin. The disclosed compositions may be utilized as soil-amendments for controlling pests, weeds and for enhancing growth of plants. The biodiesel glycerin utilized in the disclosed compositions may be treated by one or more steps including neutralization, heating, refluxing, condensing, and distilling.

20 Claims, 12 Drawing Sheets

(56) References Cited

OTHER PUBLICATIONS

Rodriguez-Kabana, R., and N. Kokalis-Burelle. 1997. Chemical and Biological Control. pp. 397-418. IN: R.J. Hillocks and J.M. Weller (eds.): Soil-Borne Diseases of Tropical Crops. CAB International. New York. pp. 452.

Rodriguez-Kabana, R., E.A. Geurtal, R.H. Walker, and D.H. Teem 2003. Nematicidal and Herbicidal Properties of 2-Propenal (Acrolein) a Potential Alternative to Methyl Bromide for Soil Fumigation. Proceedings Annual International Research Conference on Methyl Bromide Alternatives and Emissions Reductions. Nov. 3-6, 2003. San Diego, California. pp. 51-1 to 51-7.

Rodriguez-Kabana, R., L.J. Simmons, R.H. Walker, E.A Geurtal, & D.H. Teem. 2004. A Dosimetric Study on the Herbicidal Activity of Acrolein (2-Propenal). Proceedings Annual International Research Conference on Methyl Bromide Alternatives and Emissions Reductions. Oct. 31-Nov. 3, 2004. Orlando, Florida. Paper No. 22.

Whitmore, F.C. 1951. Orgnic Chemistry, vol. 1, Dover Publications, Inc. New York.

Zhang, Y., et al., "Biodiesel production from waste cooking oil: 1. Process Design and Technological Assessment", Bioresource Technology, 2003, 89: 1-16.

PCT Search Report, European Patent Office, PCT/US2008/055490, Apr. 9, 2009.

"Solubility of Urea in Water-Alcohol Mixtures," Lee, F.-M. and L. Lahi, Journal of Chemical and Engineering Data 1793): 304-306 (1982).

"Preparation of Aqueous Buffer Solutions," by Fromm, J. (1997), available at <http//www.3rd1000.com/chem 101/chem103q.htm>.

Communication for EP08743621.8 dated Jul. 25, 2014.

Elsik et al., "Glyphosate adjuvant formulation with glycerin", Journal of ASTM International, 4(5): 1.

Search Report for EP15152863 dated Jun. 10, 2015.

TREATED BIODIESEL GLYCERIN

CROSS-REFERENCE TO RELATED APPLICATIONS

This application is a continuation of U.S. patent application No. 14/886,374, filed Oct. 19, 2015, and published on Feb. 11, 2016, as U.S. Publication No. 2016/0037770, and which application is a continuation of U.S. patent application No. 14/268,381, filed May 2, 2014, and published on Sep. 25, 2014, as U.S. Publication No. 2014/0287917, and which application is a continuation of U.S. patent application No. 13/836,460, filed on Mar. 15, 2013, which published on Dec. 12, 2013, as U.S. Publication No. 2013/0331263, and issued as U.S. Pat. No. 8,754,134, on Jun. 17, 2014, and which application is a continuation of U.S. patent application No. 12/040,484, filed on Feb. 29, 2008, and published on Sep. 4, 2008, as U.S. Publication No. 2008/0214679, and issued as U.S. Pat. No. 8,519,009, on Aug. 27, 2013, and which claims the benefit of priority under 35 U.S.C. §119(e) to prior U.S. provisional application no. 60/904,672, filed on Mar. 2, 2007; application No. 60/937,128, filed on Jun. 26, 2007; application No. 60/937,243, filed on Jun. 26, 2007; and application No. 60/964,913, filed on Aug. 15, 2007; the contents of which are incorporated by reference herein in their entireties.

BACKGROUND

The field of the invention relates to glycerin by-products of biodiesel fuel production. In particular, the field of the invention related to the use of treated glycerin by-products of biodiesel fuel production as soil-amendments.

Biodiesel fuels (BDF) are important sustainable energy sources. They are available commercially for use as alternatives for replacement of fuels derived from coal, petroleum, and other fast dwindling and non-renewable fossil energy sources. BDF usually are esters of fatty acids with simple alcohols, principally methanol. The production of fatty acids for BDF manufacture may be based on a transesterification reaction of sodium methylate with animal or vegetable fats, which are esters of acids with glycerin (1,2,3-propanetriol). This is followed by separation of glycerin and other impurities from the methylated fatty acids, usually based on the fact that glycerin has a higher density than methylated fatty acids and sinks to the bottom of a batch reaction mixture. The BDF process thus results in accumulation of significant quantities of crude glycerin as by-product (i.e., "BDF glycerin").

BDF glycerin commonly contains about 65-85% glycerin and other impurities that include acrolein, monoglycerides, and "high boiling compounds." Production of commercial-grade glycerin, which is usually about 90-95% glycerin, requires removal of these impurities for potential markets. The increased cost of purification and the surfeit of glycerin in the world market today translate into a serious disposal problem for this by-product of BDF manufacture. Most crude glycerin today often is sold for burning as a source of energy. The oversupply of glycerin is considered one of the major problems in development of the biodiesel industry and new compositions and uses for BDF glycerin are desirable.

SUMMARY

Disclosed are compositions that comprise treated crude glycerin that is obtained as a by-product of methods for producing biodiesel fuel. The disclosed compositions may be useful as soil-amendments for controlling pests, controlling weeds, or enhancing growth of crops as a fertilizer. The disclosed composition may be utilized as soil-amendments either alone or in combination with additional ingredients.

In some embodiments, the disclosed compositions are utilized as soil-amendment compositions for controlling soil-bourne pests, weeds, or both, and comprise: (a) an effective amount of a treated crude glycerin composition, where the crude glycerin composition is obtained as a by-product of a reaction mixture for producing biodiesel fuel and the crude glycerin composition is treated by: (i) adjusting the pH of the crude glycerin composition to about 4.0-6.8 (preferably 5.5-6.8, and more preferably 5.8-6.5) to obtain a neutralized composition; and (ii) removing an insoluble precipitate from the neutralized composition; thereby obtaining the treated crude glycerin composition; and optionally (b) an effective amount of an nitrogen source (e.g., an organic or inorganic nitrogen source); where the composition has a molar ratio of total carbon to total nitrogen (C:N) of about (22.4-5.6):1, and preferably about (16.8-11.2):1. In further embodiments, the crude glycerin composition is further treated by: (iii) performing one or more steps that include heating, refluxing, condensing, or distilling the neutralized composition; and optionally (iv) removing or collecting a volatile distillate fraction; thereby obtaining the treated crude glycerin composition.

The disclosed compositions may be utilized as soil-amendment compositions for controlling soil-borne pests, weeds, or both. In some embodiments, the soil-borne pests are parasitic nematodes such as *Rotylenchulus reniformis*. In some embodiments, the disclosed compositions may be effective for reducing parasitic nematodes populations in amended soil by at least about 50% (preferably by at least 60%, 70%, 80%, or 90%) when applied at an application rate of about 1 ml/kg soil (or optionally at a higher rate of about 2 ml/kg soil, 3 ml/kg soil, or 4 ml/kg soil). In further embodiments, the disclosed compositions may not have a significantly detrimental effect on beneficial nematodes. For example, in some embodiments the disclosed compositions do not reduce beneficial microbivorous nematodes in amended soil by more than about 50% (preferably by no more than least 40%, 30%, 20%, or 10%) when applied at an application rate of about 1 ml/kg soil (or optionally at a higher rate of about 2 ml/kg soil, 3 ml/kg soil, or 4 ml/kg soil).

The crude glycerin utilized to prepare the disclosed compositions may be obtained as a by-product of a reaction mixture for producing biodiesel fuel (e.g., a reaction mixture for producing alkyl esters of fatty acids via transesterification). The reaction mixture for producing biodiesel fuel may include: (a) animal fat, vegetable oil, or a mixture thereof; (b) a base, wherein the reaction mixture has a pH of at least about 11; and (c) an alcohol. Suitable bases may include, but are not limited to, metal hydroxides (e.g., NaOH and KOH), metal alkoxides (e.g., $NaOCH_3$ and $KOCH_3$), and mixtures thereof. In some embodiments, the base is a potassium salt (e.g., KOH, $KOCH_3$, or mixture thereof). Suitable alcohols may include, but are not limited to, aliphatic alcohols such as methanol, ethanol, or a mixture thereof.

The crude glycerin utilized to prepare the disclosed compositions includes glycerin (e.g., at a concentration of about 65-85%) and may include additional components, which may include, but are not limited to, enal compounds (e.g., acrolein or "2-propenal"), residual glycerides (e.g., monoglycerides), and residual volatiles (e.g., alcohol such as methanol or ethanol). The crude glycerin typically is treated prior to being utilized to prepare the disclosed composition.

Prior to being treated, the crude glycerin may have a basic pH (e.g., greater than at least about 11 or 12). After being treated, the crude glycerin may have a lower pH (e.g., about 4.0-6.8, preferably about 5.5-6.8, and more preferably about 5.8-6.5). The treated crude glycerin includes glycerin (e.g., at a concentration of about 65-85%) and may include additional components, which may include, but are not limited to, enal compounds or enriched amounts of enal compounds (e.g., acrolein or "2-propenal"), reduced amounts of residual glycerides (e.g., monoglycerides), and reduced amounts of residual volatiles (e.g., alcohol such as methanol or ethanol).

In some embodiments, the pH of the crude glycerin is adjusted by adding an acid to the crude glycerin. Suitable acids include, but are not limited to, organic acids such as carboxylic acids (e.g., acetic acid, propionic acid, butyric acid, valeric acid, or mixtures thereof), inorganic acids (e.g., phosphoric acid, sulfuric acid, or mixtures thereof), or mixtures of organic acids and inorganic acids. Suitable acids may include polyhydroxycarboxylic acids (e.g., citric acid). In some embodiments, the acid is a mixture an organic acid and an inorganic acid, such as a mixture of propionic acid and phosphoric acid (preferably at a ratio of about (3-1):1 or at a ratio of about 2:1).

The disclosed compositions may be prepared from crude glycerin that includes, as an additional component, an enal compound such as acrolein (i.e., 2-propenal). The crude glycerin may be treated in order to increase the amount of enal compounds present in the crude glycerin. For example, in some embodiments, the crude glycerin may be treated by heating the crude glycerin to about 200-300° C. In other embodiments, the crude glycerin may be treated by reacting the crude glycerin with sodium bisulfate or potassium bisulfate. In some embodiments, the disclosed compositions may include at least about 1% acrolein (preferably at least about 2%, 3%, 4%, or 5% acrolein).

In some embodiments, the crude glycerin optionally is treated by performing one or more steps such as heating, refluxing, condensing, and distilling. For example, the pH of the crude glycerin may be adjusted to about 4.0-6.8 (preferably about 5.5-6.8, and more preferably about 5.8-6.5) to obtain a neutralized composition; optionally, any solid precipitate formed in the neutralized composition may be removed; and optionally, the neutralized composition may be heated to a temperature greater than about 80° C. (preferably greater than about 85° C. or greater than about 90° C.) under vacuum. A volatile distillate fraction may be removed from the composition thusly heated leaving a retained fraction. In further embodiments, the retained fraction, may be heated, refluxed, condensed, or distilled, for example, by heating the retained fraction to a temperature of about 200-300° C. (preferably about 220-250° C.) for at least about 30 minutes (preferably for about 60-90 minutes), thereby obtaining a refluxed glycerin composition. The refluxed glycerin composition optionally may be heated to temperatures ranging from about 40-250° C. and one or more distillates may be collected. In some embodiments, a distillate is collected where the distillate has a boiling point range of about 50-100° C. The refluxed glycerin and collected distillates may have an enriched concentration of enal compounds (e.g., at least about 1%, 2%, 3%, 4%, 5%, 10%, or 15% acrolein).

The disclosed composition may be utilized as soil-amendments. In some embodiments, the composition includes a treated crude glycerin composition and further may include a nitrogen source. In some embodiments, the disclosed compositions include a treated crude glycerin composition and nitrogen source and have a molar ratio of total carbon to total nitrogen (C:N) of about (22.4-5.6):1, and preferably about (16.8-11.2):1. Nitrogen sources may include organic nitrogen sources, inorganic nitrogen sources, or a mixture thereof. Suitable organic nitrogen sources may include, but are not limited to, urea, casein, and mixtures thereof. Addition suitable sources of organic nitrogen may include, but are not limited to, manure (e.g., dairy manure, cage manure including egg layers' manure, or mixtures thereof), hay (e.g., legume hay, grass hay, or mixtures thereof), and meal (e.g., alfalfa meal, soybean meal, blood meal, cottonseed meal, crab meal, fish meal, feather meal, or mixtures thereof). Suitable inorganic nitrogen sources may include, but are not limited to, ammonium salts (e.g., ammonium sulfate), nitrite salts, nitrate salts (e.g., potassium nitrate or ammonium nitrate), and mixtures thereof. Preferably, the nitrogen source may be readily assimilated by plants when the disclosed compositions are utilized as soil-amendments. The nitrogen source may be added to the treated glycerin composition as a solid or as a solution. In further embodiments, the disclosed compositions do not include a nitrogen source and may be added to soil as an amendment in order to achieve in the amended soil a molar ratio of total carbon to total nitrogen (C:N) of about (22.4-5.6):1, and preferably about (16.8-11.2):1, where the soil, prior to amendment, includes a nitrogen source.

The disclosed compositions typically include a treated crude glycerin composition and further may include additional components that are suitable as soil-amendments. For example the disclosed compositions may include additional components such as pesticides (e.g., nematocides, insecticides, fungicides, and herbicides), fertilizers, or both. In some embodiments, the disclosed compositions include a treated crude glycerin composition and further include a sulfur compound.

Also disclosed are methods for preparing the disclosed compositions. In some embodiments, the disclosed methods include methods for preparing a soil-amendment composition for controlling soil-borne pests, weeds, or both, and may include the steps of (i) adjusting the pH of a crude glycerin composition to about 4.0-6.8 (preferably 5.5-6.8, and more preferably 5.8-6.5) to obtain a neutralized composition, where the crude glycerin composition is obtained as a by-product of a reaction mixture for producing biodiesel fuel; and (ii) removing an insoluble precipitate from the neutralized composition; thereby obtaining the treated crude glycerin composition. The treated crude glycerin composition may be utilized as a soil-amendment composition or optionally further may be treated (e.g., subjected to heating, refluxing, condensation, or distillation) or further may be combined with additional ingredients (e.g., a nitrogen source). In some embodiments, the crude glycerin composition is further treated by: (iii) performing one or more steps such as heating, refluxing, condensing, and distilling the neutralized composition; and optionally (iv) removing or collecting a volatile distillate fraction; thereby obtaining the treated crude glycerin composition suitable for use as a soil-amendment composition. In further embodiments, the treated crude glycerin composition further is combined with an effective amount of nitrogen source; wherein the composition has a molar ratio of total carbon to total nitrogen (C:N) of about (22.4-5.6):1, and preferably of about (16.8-11.2):1.

Also disclosed are methods for controlling soil-borne pests, weeds, or both. The methods may include applying the disclosed compositions as a liquid soil-amendment composition at an application rate of at least about 1 ml/kg soil (optionally at an application rate of at least about 2 ml/kg soil, 3 ml/kg soil, or 4 ml/kg soil). The selected application rates may achieve an effective concentration of acrolein in soil for controlling pest, weeds, or both (e.g., at least about 25 mg acrolein/kg soil, 50 mg acrolein/kg soil, 100 mg acrolein/kg soil, 200 mg acrolein/kg soil, or 300 mg acrolein/kg soil). The soil-amendment composition may comprise an effective amount of a treated crude glycerin composition, where the crude glycerin composition is obtained as a by-product of a reaction mixture for producing biodiesel fuel and the crude glycerin composition is treated by: (i) adjusting the pH of the crude glycerin composition to about 4.0-6.8 (preferably 5.5-6.8, and more preferably 5.8-6.5) to obtain a neutralized composition; and (ii) removing an insoluble precipitate from the neutralized composition; thereby obtaining the treated crude glycerin composition. Optionally, the crude glycerin composition may be further treated by (iii) performing one or more steps such as heating, refluxing, condensing, and distilling the neutralized composition; and optionally (iv) removing or collecting a volatile distillate fraction; thereby obtaining the treated crude glycerin composition. Optionally, the soil-amendment further comprises an effective amount of an organic nitrogen source; where the soil-amendment composition has a molar ratio of total carbon to total nitrogen (C:N) of about (22.4-5.6):1, and preferably of about (16.8-11.2):1.

DETAILED DESCRIPTION

Figure 1:
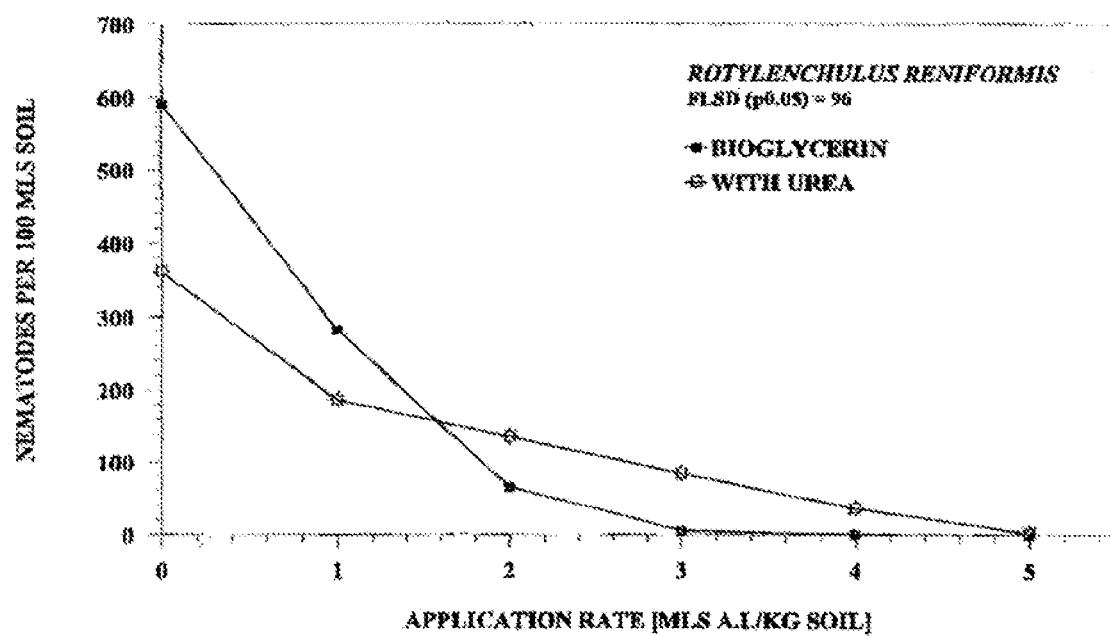
FIG. 1. The effect of a neutralized bioglycerin composition (see Example 1) at various application rates (0 ml/kg soil, 1 ml/kg soil, 2 ml/kg soil, 3 ml/kg soil, 4 ml/kg soil, or 5 ml/kg soil) with or without added urea (150 mg/kg soil) on nematode population (*Rotylenchulus reniformis*/100 ml soil) was assessed.
Figure 2:
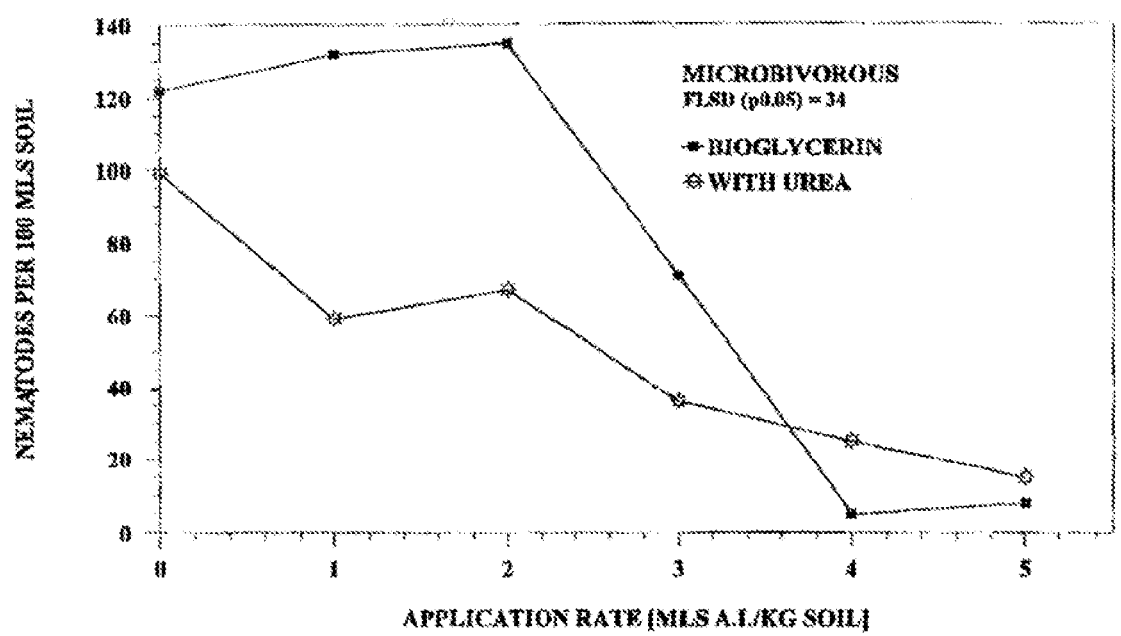
FIG. 2. The effect of a neutralized bioglycerin composition (see Example 1) at various application rates (0 ml/kg soil, 1 ml/kg soil, 2 ml/kg soil, 3 ml/kg soil, 4 ml/kg soil, or 5 ml/kg soil) with or without urea (150 mg/kg soil) on nematode population (Microbivorous/100 ml soil) was assessed.
Figure 3:
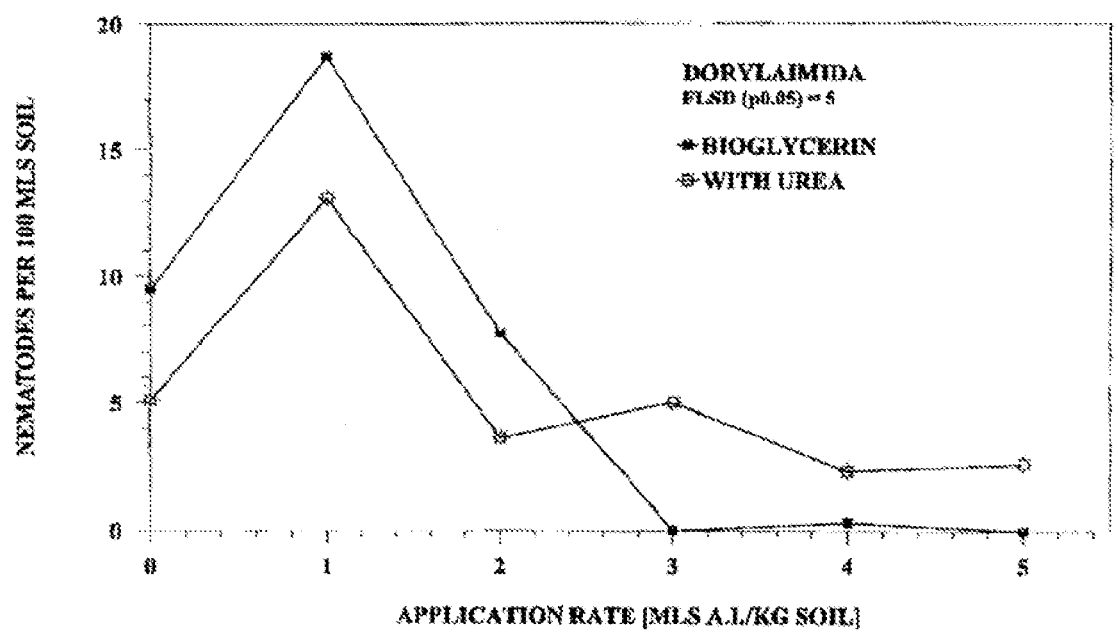
FIG. 3. The effect of a neutralized bioglycerin composition (see Example 1) at various application rates (0 ml/kg soil, 1 ml/kg soil, 2 ml/kg soil, 3 ml/kg soil, 4 ml/kg soil, or 5 ml/kg soil) with or without urea (150 mg/kg soil) on nematode population (Dorylaimida/100 ml soil) was assessed.
Figure 4:
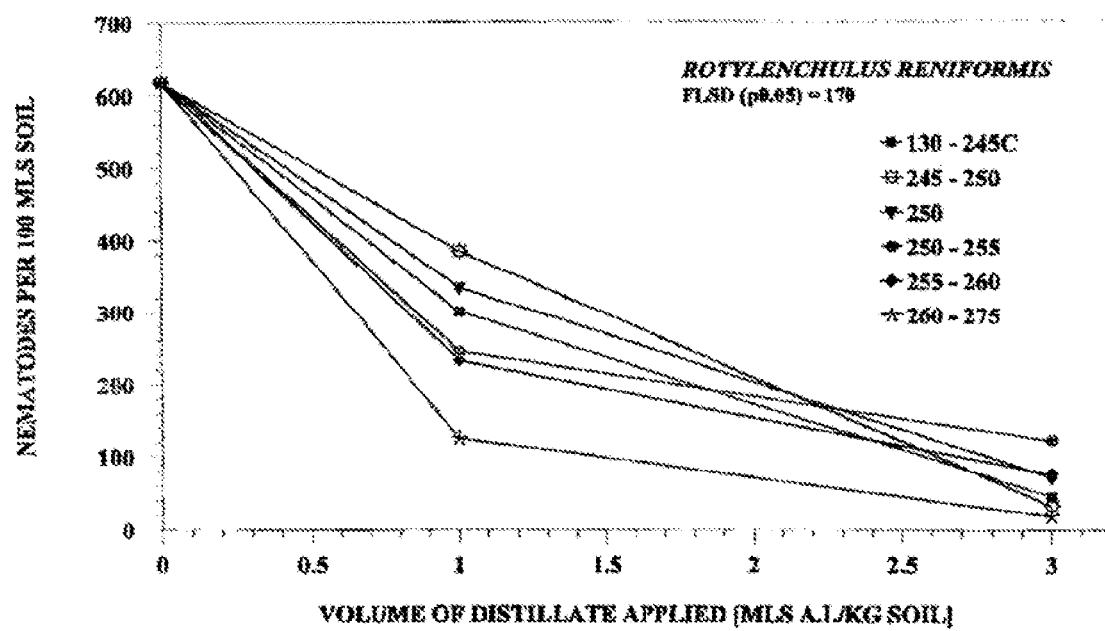
FIG. 4. The effect of distilled fractions of neutralized bioglycerin compositions (see Examples 1-3, fractions collected at 130-245° C., 245-250° C., 250° C., 250-255° C., 255-260° C., and 260-275° C.) at various application rates (0 ml/kg soil, 1 ml/kg soil, or 3 ml/kg soil) on nematode population (*Rotylenchulus reniformis*/100 ml soil) was assessed.
Figure 5:
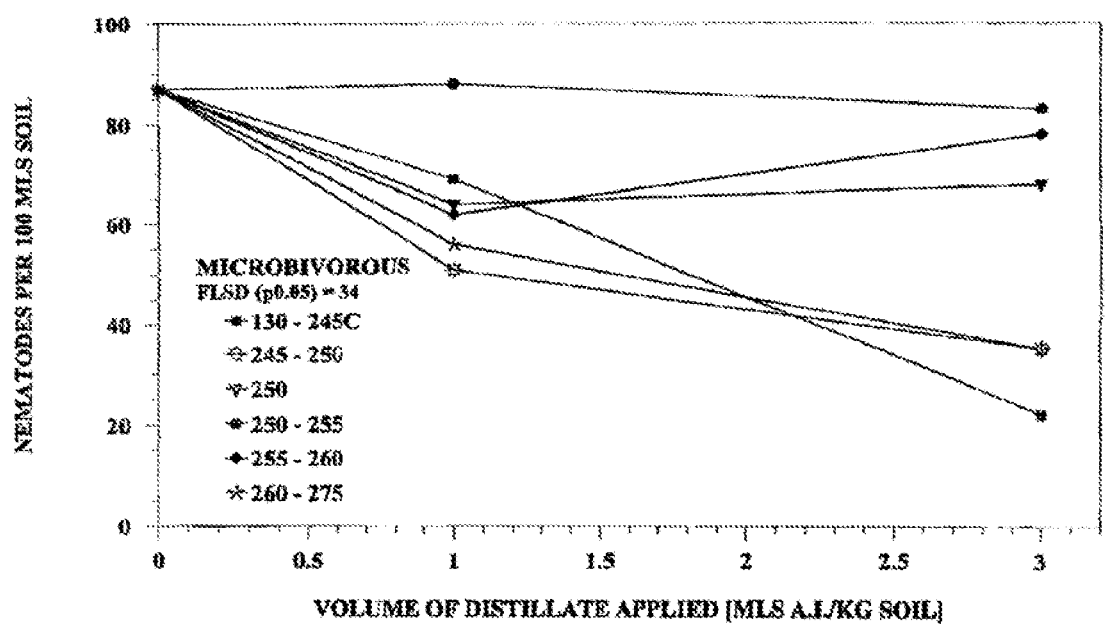
FIG. 5. The effect of distilled fractions of neutralized bioglycerin compositions (see Examples 1-3, fractions collected at 130-245° C., 245-250° C., 250° C., 250-255° C., 255-260° C., and 260-275° C.) at various application rates (0 ml/kg soil, 1 ml/kg soil, or 3 ml/kg soil) on nematode population (Microbivorous/100 ml soil) was assessed.
Figure 6:
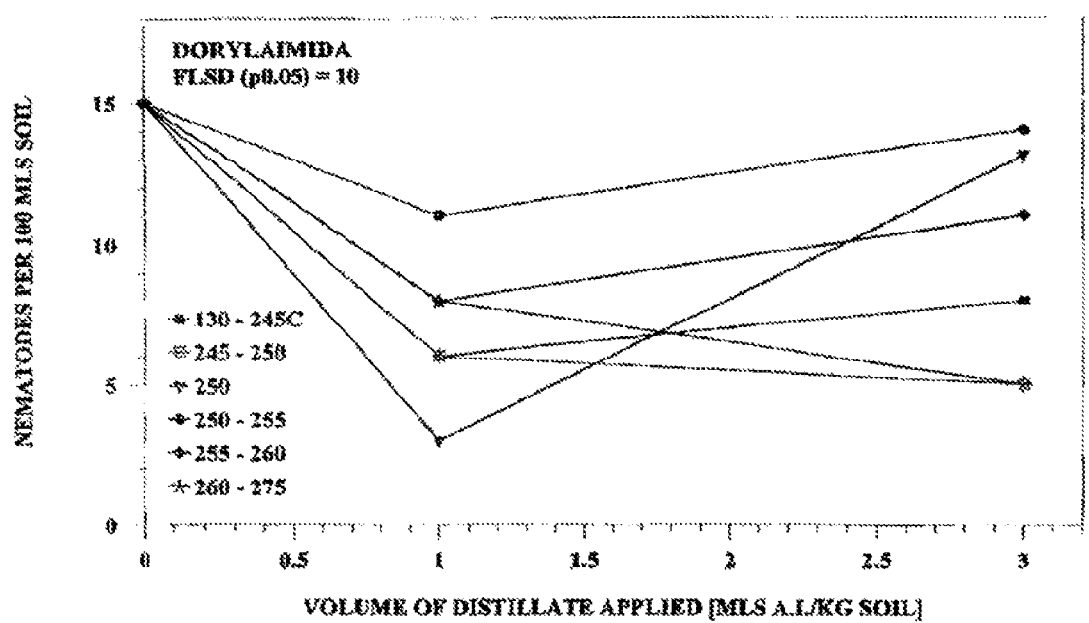
FIG. 6. The effect of distilled fractions of neutralized bioglycerin compositions (see Examples 1-3, fractions collected at 130-245° C., 245-250° C., 250° C., 250-255° C., 255-260° C., and 260-275° C.) at various application rates (0 ml/kg soil, 1 ml/kg soil, or 3 ml/kg soil) on nematode population (Dorylaimida/100 ml soil) was assessed.
Figure 7:
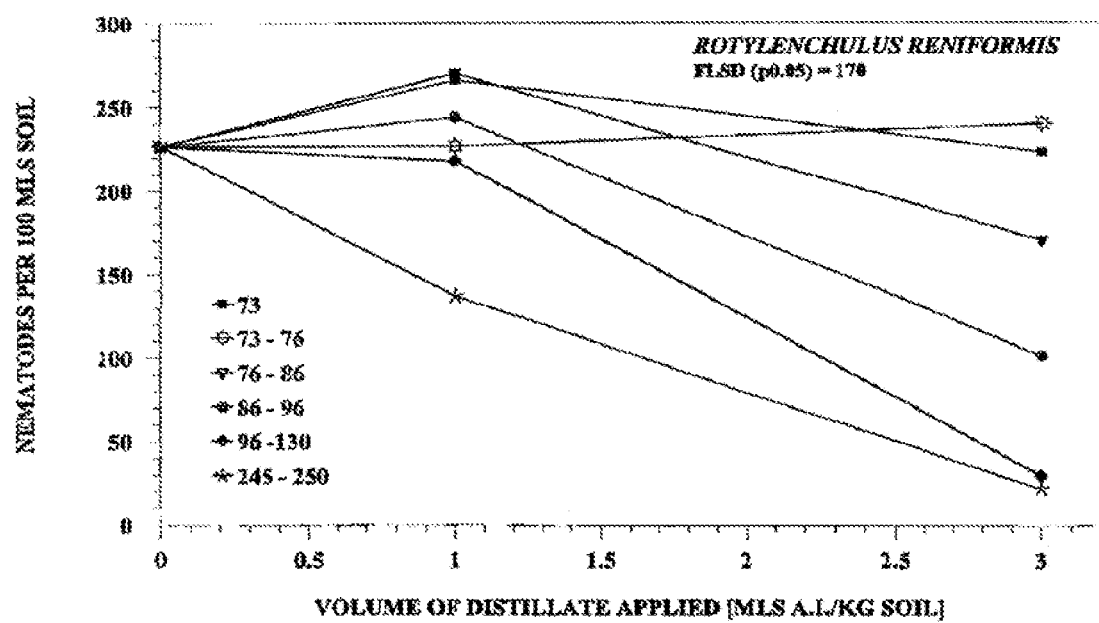
FIG. 7. The effect of distilled fractions of neutralized bioglycerin compositions (see Examples 1-3, fractions collected at 73° C., 73-76° C., 76-86° C., 86-96° C., 96-130° C., and 245-250° C.) at various application rates (0 ml/kg soil, 1 ml/kg soil, or 3 ml/kg soil) on nematode population (*Rotylenchulus reniformis*/100 ml soil) was assessed.
Figure 8:
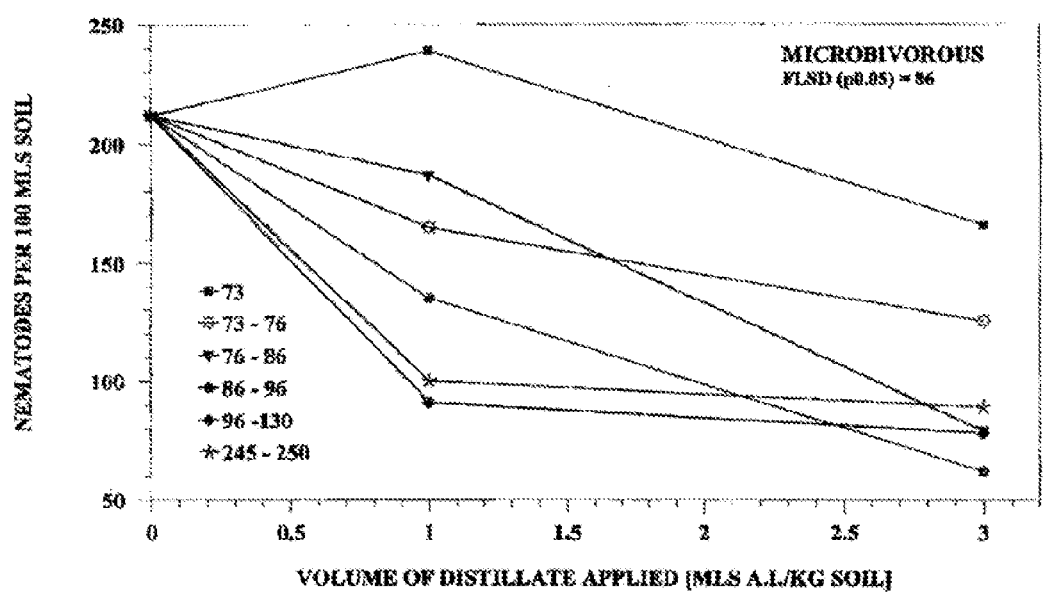
FIG. 8. The effect of distilled fractions of neutralized bioglycerin compositions (see Examples 1-3, fractions collected at 73° C., 73-76° C., 76-86° C., 86-96° C., 96-130° C., and 245-250° C.) at various application rates (0 ml/kg soil, 1 ml/kg soil, or 3 ml/kg soil) on nematode population (Microbivorous/100 ml soil) was assessed.
Figure 9:
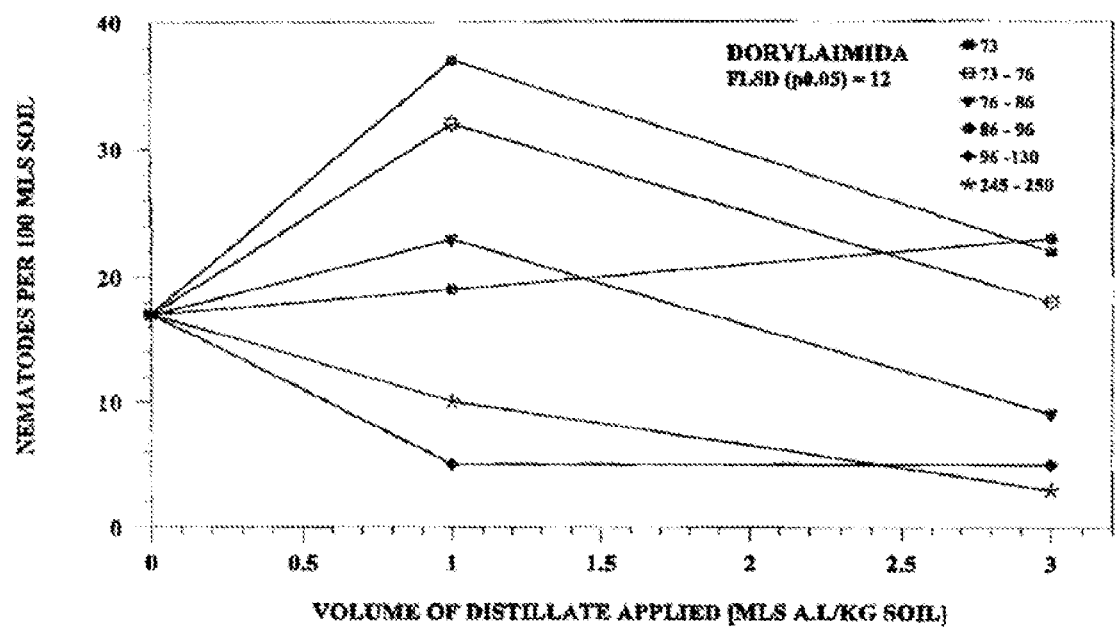
FIG. 9. The effect of distilled fractions of neutralized bioglycerin compositions (see Examples 1-3, fractions collected at 73° C., 73-76° C., 76-86° C., 86-96° C., 96-130° C., and 245-250° C.) at various application rates (0 ml/kg soil, 1 ml/kg soil, or 3 ml/kg soil) on nematode population (Dorylaimida/100 ml soil) was assessed.
Figure 10:
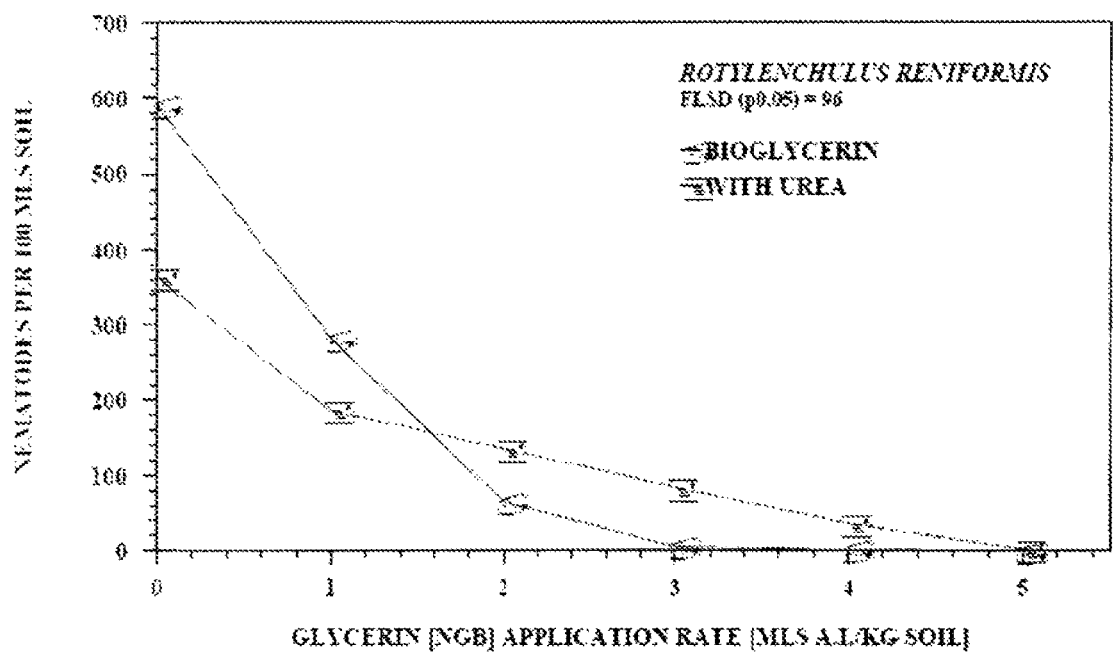
FIG. 10. The effect of a neutralized bioglycerin composition (see Example 1) at various application rates (0 ml/kg soil, 1 ml/kg soil, 2 ml/kg soil, 3 ml/kg soil, 4 ml/kg soil, or 5 ml/kg soil) with or without added urea (150 mg/kg soil) on nematode population (*Rotylenchulus reniformis*/100 ml soil) was assessed.

The present invention is described herein using several definitions, as set forth below and throughout the application.

Unless otherwise specified, the terms "a" or "an" mean "one or more."

As used herein, "about" and "substantially" will be understood by persons of ordinary skill in the art and will vary to some extent on the context in which they are used. If there are uses of the term which are not clear to persons of ordinary skill in the art given the context in which it is used, "about" will mean up to plus or minus 10% of the particular term and "substantially" will mean more than plus or minus 10% of the particular term.

As used herein, "crude glycerin," "biodiesel glycerin," "biodiesel fuel glycerin," "BDF glycerin," or "bioglycerin" refer to a glycerin composition that is obtained as a by-product of a reaction for producing biodiesel fuel (BDF), and which may be further treated or left untreated. The reaction for producing BDF may include a transesterification reaction or alcoholysis reaction that occurs in a basic reaction mixture (e.g., having a pH greater than about 11) comprising triglycerides (e.g., which are present in animal or vegetable fats or oils) and alcohol (e.g., methanol or ethanol). The reaction mixture may produce fatty acid alkyl esters (e.g., fatty acid methyl esters) and glycerin. As used herein, "glycerin," "glycerine," or "glycerol" refers to the compound 1,2,3, propanetriol.

The disclosed compositions may include liquid compositions. Unless indicated as otherwise, percentage concentrations refer to percentage on a volume/volume basis.

The disclosed compounds may be utilized as soil-amendments. Glycerin is not only a good carbon source for some microorganisms in soil but BDFs glycerin also contain acrolein, potentially a desirable component in development of glycerin-based organic amendments. The heating of glycerin at to high temperatures results in dehydration, re-arrangement and formation of enal compounds such as acrolein (i.e., "2-propenal") (Merck Index. 1989. 11$^{th}$ Edition. Merck & Co., Inc. Rahwayt, J. J. U.S.A.; and Whitmore, F. C. 1951. Orgnic Chemistry. Vol. 1. Dover Publications, Inc. New York; incorporated by reference herein in their entireties). Acrolein is a toxic compound registered for use in control of aquatic weeds (Meister Pro. 2006. Crop Protection Handbook. Moister Media, Willoughby, Ohio, incorporated by reference herein in its entirety). Research at Auburn University has demonstrated that acrolein has fungicidal and nematocidal activities in greenhouse and field experiments (Belcher, J. L., R. H. Walker, R. Rodriguez-Kabana, E. Guertal, and L. E. Simmons, 2005, Proceedings Annual International Research Conference on Methyl Bromide Alternatives and Emissions Reductions, Oct. 31-Nov. 3, 2004, San Diego, Calif., Paper No. 24; Belcher, J. L., R. H. Walker, and K Rodriguez-Kabana, 2004, Proceedings Annual International Research Conference on Methyl Bromide Alternatives and Emissions Reductions, Oct. 31-Nov. 3, 2004, Orlando, Fla., Paper No. 23; Rodriguez-Kabana et al., U.S. patent application Ser. No. 11/260,771, filed Oct. 27, 2005; Rodriguez-Kabana, R, L. J. Simmons, R. H. Walker, E. A. Guertal, & D. H. Teem, 2004, Proceedings Annual International Research Conference on Methyl Bromide Alternatives and Emissions Reductions, Oct. 31-Nov. 3, 2004, Orlando, Fla. Paper No. 22; Rodriguez-Kabana, R., E. A. Guertal, R. H. Walker, and D. H. Teem, 2003, Proceedings Annual International Research Conference on Methyl Bromide Alternatives and Emissions Reductions, Nov. 3-6, 2003, San Diego, Calif., Pages 51-1 to 51-7; incorporated herein by reference in their entireties).

The disclosed compositions may include enal compounds. Enal compounds may include dehydration products of glycerol compounds. As used herein, enal compounds include 2-propenal (i.e., acrolein) and polymers thereof. In some embodiments, the disclosed compositions may include at least about 1%, 2%, 3%, 4%, 5%, 10%, or 15% 2-propenal and polymers thereof.

The disclosed compositions may include treated glycerin compositions and may be used as soil-amendments that exhibit fertilizing activity. For example, the disclosed compositions may include one or more of assimilable potassium, phosphorus, and nitrogen. In some embodiments, the treated glycerin composition is prepared from a crude glycerin composition that is obtained from a transesterification reaction in which a potassium salt is used as a catalyst or a basifying agent (e.g., KOH or KOCH$_3$). In further embodiments, the crude glycerin composition is treated with a phosphorus-containing acid (e.g., phosphoric acid or phosphorous acid). In even further embodiments, a nitrogen source may be added to the treated glycerin composition to provide a soil-amendment composition having a suitable C:N ratio.

Incorporation into soil of organic matter with the appropriate C:N ratio is one of the best methods to suppress plant parasitic nematodes and other soil-borne pests. Stimulation of microbial activities in soil following incorporation of organic amendments has been repeatedly demonstrated to results in control of plant parasitic nematodes, a number of phytopathogenic fungi and even some insects and weeds. (Rodriguez-Kabana, R, and M. H. Pope, Nematropica 11: 175-186 (1986); Rodriguez-Kabana, R., G. Morgan-Jones, and T. Chet. 1987. Plant and Soil 100: 237-247; Stirling, G. K 1991. Biological control of plant parasitic nematodes: progress, problem and prospects. Wallingford, Oxon, UK, CAB International, pp. 282; incorporated herein by reference in their entireties). Considerable research has been directed to the preparation of organic amendments based on agricultural wastes and other by-products of human activities, e.g., chicken and other manures, sewage and other urban ordures, in order to dispose of these materials in an environmentally acceptable manner (Stirling, 1991). In some embodiments, the disclosed compositions include a nitrogen source which may be an organic nitrogen source or an inorganic nitrogen source. Preferably, the nitrogen source is soluble in glycerin. The disclosed compositions may have a suitable C:N ratio (e.g., a C:N ration that about (22.4-5.6):1 or about (16.8-11.2):1).

As used herein, the phrase "effective amount" or "effective rate" shall mean that amount or rate that provides the specific response for which the composition is applied in a significant number of applications. The disclosed compositions may include an effective amount of the treated glycerin compositions to achieve a pesticidal effect (e.g., a nematocidal, a fungicidal, an herbicidal, or insecticidal effect) when applied at a given application rate. In some embodiments, the treated glycerin compositions may include enal compounds (e.g., 2-propenal). Effective amounts of enal compounds (e.g., 2-propenal) and effective application rates for compositions that comprise enal compounds for controlling pests and weeds are disclosed in U.S. patent application Ser. No. 11/260,771, which is incorporated herein by reference in its entirety. In some embodiments, the disclosed compositions include 2-propenal and are applied to soil as an amendment at an application rate that achieves an effective concentration of 2-propenal of at least about 25 mg/kg soil (or at least about 50 mg/kg soil, 100 mg/kg soil, 200 mg/kg soil, or 300 mg/kg soil).

The disclosed compositions may be utilized to control one or more pests (e.g. parasitic nematodes, fungi, and weeds). In some embodiments, the disclosed compositions are applied to soil at a given rate (e.g., about 1 ml/kg soil, about 2 ml/kg soil, about 3 ml/kg soil, or about 4 ml/kg soil) and reduce the pest population in the soil (e.g., parasitic nematodes as measured by number of pests/mls soil) by at least about 50% (or at least about 60%, 70%, 80%, or 90%). In further embodiments, the disclosed compositions do not significantly reduce the population of beneficial nematodes present in the soil (e.g., microbivores), where the disclosed composition are applied to soil at a given rate (e.g., about 1 ml/kg soil, about 2 ml/kg soil, about 3 ml/kg soil, or about 4 ml/kg soil) and do not reduce the beneficial nematode population in the soil by more than about 50% (or no more than about 40%, 30%, 20%, or 10%).

ILLUSTRATIVE EMBODIMENTS

The following list of embodiments is illustrative and is not intended to limit the scope of the claimed subject matter.

Embodiment 1. A soil-amendment composition for controlling soil-borne pests, the composition comprising: (a) an effective amount of a treated crude glycerin composition, wherein the crude glycerin composition is obtained as a by-product of a reaction mixture for producing biodiesel fuel and the crude glycerin composition is treated by: (i) adjusting the pH of the crude glycerin composition to about 4.0-6.8 to obtain a neutralized composition; and (ii) removing an insoluble precipitate from the neutralized composition; thereby obtaining the treated crude glycerin composition; and (b) an effective amount of a nitrogen source; wherein the composition has a molar ratio of total carbon to total nitrogen (C:N) of about (22.4-5.6):1, preferably about (16.8-11.2):1.

Embodiment 2. The soil-amendment composition of embodiment 1, wherein the crude glycerin composition is further treated by: (iii) heating the neutralized composition; and (iv) removing a volatile distillate fraction from the neutralized composition; thereby obtaining the treated crude glycerin composition.

Embodiment 3. The soil-amendment composition of embodiment 2, wherein the crude glycerin composition is further treated by: (v) refluxing the neutralized composition; and (vi) distilling and collecting a volatile distillate fraction; thereby obtaining the treated crude glycerin composition.

Embodiment 4. The composition of any of embodiments 1-3, wherein the soil-borne pests are parasitic nematodes.

Embodiment 5. The composition of any of embodiments 1-4, wherein the composition is effective for reducing parasitic nematodes by at least about 50% when applied at an application rate of about 1 ml/kg soil.

Embodiment 6. The composition of any of embodiments 1-5, wherein the composition does not reduce microbivorous nematodes by more than about 50% when applied at an application rate of about 1 ml/kg soil.

Embodiment 7. The composition of any of embodiments 1-6, wherein the reaction mixture for producing biodiesel fuel comprises: (a) animal or vegetable fats or oils, or a mixture thereof; (b) a base, wherein the reaction mixture has a pH of at least about 11; and (c) an alcohol.

Embodiment 8. The composition of embodiment 4, wherein the base is selected from the group consisting of NaOH, KOH, NaOCH$_3$ and KOCH$_3$.

Embodiment 9. The composition of embodiment 4, wherein the alcohol is methanol or ethanol.

Embodiment 10. The composition of any of embodiments 1-9, wherein prior to being treated the crude glycerin composition comprises: (a) about 65-85% glycerin; (b) acrolein; (c) monoglycerides; and (d) alcohol; and the crude glycerin composition has a pH of greater than about 11.

Embodiment 11. The composition of any of embodiments 1-10, wherein the treated crude glycerin composition comprises: (a) about 65-85% glycerin; and (b) acrolein; and (c) no more than about 10% monoglycerides (preferably no more than about 8%, 6%, 4%, or 2% monoglycerides).

Embodiment 12. The composition of embodiment 2, wherein the treated crude glycerin composition comprises: (a) about 65-85% glycerin; and (b) acrolein; and (c) no more than about 15% alcohol (preferably no more than about 10% or 5% alcohol).

Embodiment 13. The composition of embodiment 3, wherein the treated crude glycerin composition comprises: (a) about 65-85% glycerin; and (b) at least about 5% acrolein (preferably at least about 10% or 15% acrolein).

Embodiment 14. The composition of any of embodiments 1-13, wherein adjusting the pH of the crude glycerin composition to about 4.0-6.8 comprises adding an acid to the composition.

Embodiment 15. The composition of embodiment 14, wherein the acid is an organic acid.

Embodiment 16. The composition of embodiment 14, wherein the organic acid is a carboxylic acid.

Embodiment 17. The composition of embodiment 16, wherein the carboxylic acid is acetic acid, propionic acid, butyric acid, or a mixture thereof.

Embodiment 18. The composition of embodiment 14, wherein the organic acid is a polyhydroxy carboxylic acid.

Embodiment 19. The composition of embodiment 18, wherein the polyhydroxy carboxylic acid is citric acid.

Embodiment 20. The composition of embodiment 14, wherein the acid is an inorganic acid.

Embodiment 21. The composition of embodiment 20, wherein the inorganic acid is phosphoric acid or sulfuric acid (preferably phosphoric acid).

Embodiment 22. The composition of embodiment 14, wherein the acid is a mixture of an organic acid and an inorganic acid.

Embodiment 23. The composition of embodiment 2, wherein heating comprises heating the neutralized composition to a temperature of at least about 80° C. (preferably at least about 80° C. or 90° C.) under vacuum, preferably at least about 500 mm Hg (19 inch Hg), 600 mm Hg (23 inch Hg), or 700 mm Hg (27 inch Hg).

Embodiment 24. The composition of embodiment 3, wherein refluxing comprises heating the neutralized composition to a temperature of about 200-350° C. (preferably at a temperature of about 200-300° C. or about 220-250° C.) through a condenser; and distilling comprises heating the neutralized composition and collecting distillates through a temperature range of about 40-250° C.

Embodiment 25. The composition of any of embodiments 1-24, wherein the nitrogen source is an organic nitrogen source (e.g., urea, casein, or a mixture thereof).

Embodiment 26. The composition of any of embodiments 1-25, wherein the crude glycerin composition further is treated by reacting the composition with sodium bisulfate or potassium bisulfate.

Embodiment 27. The composition of any of embodiments 1-26, further comprising sulfur.

Embodiment 28. A method for preparing a soil-amendment composition for controlling soil-borne pests, the method comprising combining: (a) an effective amount of a treated crude glycerin composition, wherein the crude glycerin composition is obtained as a by-product of a reaction mixture for producing biodiesel fuel and the crude glycerin composition is treated by: (i) adjusting the pH of the crude glycerin composition to about 4.0-6.8 to obtain a neutralized composition; and (ii) removing an insoluble precipitate from the neutralized composition; thereby obtaining the treated crude glycerin composition; and (b) an effective amount of an organic nitrogen source; wherein the composition has a molar ratio of total carbon to total nitrogen (C:N) of about (22.4-5.6):1, preferably about (16.8-11.2):1.

Embodiment 29. The method of embodiment 28, wherein the crude glycerin composition is further treated by: (iii) heating the neutralized composition; and (iv) removing a volatile distillate fraction from the neutralized composition; thereby obtaining the treated crude glycerin composition.

Embodiment 30. The method of embodiment 29, wherein the crude glycerin composition is further treated by: (v) refluxing the neutralized composition; and (vi) distilling and collecting a volatile distillate fraction; thereby obtaining the treated crude glycerin composition.

Embodiment 31. A method for preparing a soil-amendment composition for controlling soil-borne pests, the method comprising: (a) adjusting the pH of a crude glycerin composition to about 4.0-6.8 to obtain a neutralized composition; wherein the crude glycerin composition is obtained as a by-product of a reaction mixture for producing biodiesel fuel; (b) removing an insoluble precipitate from the neutralized composition, thereby obtaining a treated crude glycerin composition; and (c) combining an effective amount of the treated crude glycerin composition and an effective amount of an organic nitrogen source such that the composition has a molar ratio of total carbon to total nitrogen (C:N) of about (22.4-5.6):1, preferably about (16.8-11.2):1.

Embodiment 32. The method of embodiment 31, further comprising heating the neutralized composition; and removing a volatile distillate fraction from the neutralized composition; thereby obtaining the treated crude glycerin composition.

Embodiment 33. The method of embodiment 32, further comprising refluxing the neutralized composition; and distilling and collecting a volatile distillate fraction; thereby obtaining the treated crude glycerin composition.

Embodiment 34. A method for controlling soil-borne pests comprising applying a liquid soil-amendment composition at an application rate of at least about 1 ml/kg soil, the soil-amendment composition comprising: (a) an effective amount of a treated crude glycerin composition, wherein the crude glycerin composition is obtained as a by-product of a reaction mixture for producing biodiesel fuel and the crude glycerin composition is treated by: (i) adjusting the pH of the crude glycerin composition to about 4.0-6.8 to obtain a neutralized composition; and (ii) removing an insoluble precipitate from the neutralized composition; thereby obtaining the treated crude glycerin composition; and (b) an effective amount of an organic nitrogen source; wherein the composition has a molar ratio of total carbon to total nitrogen (C:N) of about (22.4-5.6):1, preferably about (16.8-11.2):1.

Embodiment 35. The method of embodiment 34, wherein the crude glycerin composition is further treated by: (iii) heating the neutralized composition; and (iv) removing a volatile distillate fraction from the neutralized composition; thereby obtaining the treated crude glycerin composition.

Embodiment 36. The method of embodiment 35, wherein the crude glycerin composition is further treated by: (v) refluxing the neutralized composition; and (vi) distilling and collecting a volatile distillate fraction; thereby obtaining the treated crude glycerin composition.

EXAMPLES

The following examples are illustrative and are not intended to limit the scope of the claimed subject matter.

Example 1

Neutralization of Crude Glycerin Product (CGP) from Biodiesel Production

A crude glycerin product (CGP) is produced from a transesterification reaction between sodium (or potassium) methylate and vegetable or animal oils or fats (i.e., glycerin esters of fatty acids). The transesterification reaction produces biodiesel (i.e., methyl esters of the fatty acids) and about 12-14% CGP. The pH of CGP is typically in the range of 11.5-12.5 and most commonly 12.00. Use of the CGP in agriculture requires lowering of pH to within an acceptable level for addition to soil (e.g., a pH of about 5.8-6.5).

Procedure. CGP was obtained from Alabama Biodiesel Corporation, Moundville, Ala., producers of biodiesel from food grade soybean oil. In the typical laboratory procedure, 32 mls of propionic acid are added slowly in 5-8 ml aliquots while stirring into filtered and clear 500 mls CGP. A final pH of 6.5 is attained. During the neutralization process, when the pH nears about 8.00, a clouding is observed due to precipitation of free long-chained fatty acids. These acids are either present in the vegetable oil or may be formed during the trans-methylation reaction—the acids react with $Na^+$ or $K^+$ cations to form fatty acid salts (i.e., soaps). On standing overnight (10-14 hrs) at room temperature (20-23° C.), the soaps float to the surface of the neutralized mixture and are separated from the clear underlying neutralized bioglycerin (NBG). The amount of soap collected amounts to some 10-15% of the final volume when propionic acid is used.

Other acids that can be used and the amount needed for neutralization (parenthesis) of 500 mls CGP to pH 6.5 are: glacial acetic (17 mls); butyric acid (30 mls); valeric acid (38 mls); citric acid (19 gms); 96% sulfuric acid (7 mls); 85% phosphoric acid (14 mls). The amount of soap formed varies considerably among the acids. The preferred organic acids are acetic acid and propionic acid. The preferred inorganic acid is phosphoric acid. A 2:1 mixture of (propionic acid):(phosphoric acid) is preferred when NBG is to be used as an organic amendment to soil—phosphoric acid providing the necessary phosphorus for microbial metabolism and plant growth.

NBG thus prepared can be added directly to soil for control of nematodes and other soil-borne pests. (See Example 4 and FIGS. 1-3 and 10-12.) It typically contains by volume: glycerin (~73%), recoverable volatiles (~23%), and unrecoverable volatiles (4%). The amount of glycerin and volatiles will vary with the type of oil or fat used to make biodiesel and the acid used to neutralize CGP.

Example 2

Removal of Volatile Components from Neutralized Bioglycerin (NBG)

Neutralized bioglycerin (NBG) contains significant amounts of volatile compounds that preferably are removed prior to thermal reduction of glycerin (i.e., refluxing) and formation of acrolein (i.e., 2-propenal) and related enal compounds with pesticidal properties. (See pending U.S. application Ser. No. 11/260,771, which content is incorporated herein by reference in its entirety).

Procedure. 500 mls NBG are placed in a 2 L round bottom flask which is connected to a rotary evaporator (Evapotec, Haaken Buehler) and lowered into a water bath set with water at 90° C. The flask is then rotated at 200 rpm and vacuum is applied at −700 mm Hg (−27 inch Hg) while cool water (5° C.) is run through the condenser coils. Volatiles are collected in a 1 L round bottom flask attached to bottom of the condenser section of the apparatus. The operation is stopped after approx. 30 min when 95-98% of volatiles are collected. The glycerin in the 2 L flask is now essentially free of low boiling compounds and is ready for refluxing and thermal reduction and distillation. Volatiles collected consist of methanol, and residual propionic acid, esters, and turpentine-like smelling compounds of unknown identity.

Example 3

Refluxing and Distillation of Neutralized Bioglycerin (NBG)

Condensation and reduction of glycerin occurs in nature during the burning of fats and oils. The process results in formation of acrolein (i.e., 2-propenal) and polymers thereof. These enal compounds because of their conjugate double bond with aldehyde group are very reactive and have a strong broad-spectrum of pesticidal activities (weeds, nematodes, fungi . . . etc.). The reduction and condensation of glycerin can be catalyzed by strong acids (especially $H_2SO_4$ or $NaHSO_4$). Acid, however, may not be required if the glycerin is heated at temperatures of about 200-300° C. In this manner, it is possible to enrich "stripped NBG" of its acrolein content and increase its pesticidal properties. "Stripped NBG" refers to NBG having reduced volatiles after having performed the method described in Example 2.

Procedure. Step 1. 500 mls of stripped NBG is placed in a 2 L round-bottom flask in a Barnstead Magnistir variable heater and heated to about 110° C. for about 15-20 min while stirring vigorously. This step helps reduce or eliminate any residual water. A Liebig type condenser is then fitted upright into the neck of the 2 L flask, cool water (about 5-10° C.) is run through the condenser and the temperature is gradually increased to about 220-250° C.; the liquid thus being refluxed is kept stirred vigorously for about 60-90 min while manipulating the temperature to avoid foaming. At the end of the refluxing period, the temperature is slowly reduced to less than about 40° C. and the condenser is carefully removed. A brown to dark liquid with a lachrymatory acrid vapor (producing tears) should be present in the flask.

Step 2. The 2 L flask with reduced glycerin from step 1 and still in the heater, is now connected to a simple column distillation apparatus. The temperature is gradually increased and distillates are collected through a temperature [T] range of about $40 \leq T < 250°$ C. The distilled fraction can be added directly to soil for control of nematodes and other soil-borne pests. (See Example 4 and FIGS. 4-9).

Comments. Removal of soaps after neutralization of CGP may be essential to avoid excessive foaming. The pH of stripped NBG preferably should be on the acid side, preferably in the range of about 4.5-5.5. If necessary this can be attained by adjusting the pH with $H_3PO_4$. The chemical composition of the various distillates is quite varied and at this point not completely elucidated. They all contain some acrolein with most of that compound distilling over in the range of about 50-100° C. Higher boiling distillates are presumed to be polymers of the compound as well as other chemically reduced unknown entities.

Example 4

Use of Treated Crude Glycerin Products as Soil Amendments

Objective 1. Factorial greenhouse experiments will be established to determine the efficacy of glycerin containing increasing concentrations of acrolein for control of the reniform nematode (*Rotylenchulus reniformis*), and of common damping off and seedling disease fungi (*Rhizoctonia solani*, and species of *Pythium* and *Fusarium*). Soils for these experiments will be naturally infested with the pathogens and obtained from fields known to be infected with nematodes or fungi. In each experiment, the moist soil (60% field capacity) will be apportioned in 1 kg amounts contained in 1 L cylindrical PVC pots with 1 mm mesh non-metal screen bottoms. Glycerin-acrolein mixtures will be delivered by drenching in 100 mls aqueous solutions/pot (equivalent to 1 acre inch water). Immediately after treatment, the pots will be covered with polyethylene bags (2 mil) and placed on a greenhouse bench. The bags will be removed after 2 wks and soil samples will be taken for nematological analyses by the salad bowl incubation technique (Rodriguez-Kabana & Pope, Nematropica 11:175-186 (1987)). "Hutchenson" soybean (reniform nematode susceptible) will be planted (5 seed/pot) and allowed to grow for 6 weeks when the plants will be removed and data collected on: number of surviving plants, phytotoxicity, and plant growth parameters (shoot height and weights of shoots and roots), and nematode populations in soil and root systems (salad bowl incubation).

In experiments with fungal pathogens, 20 annual morning glory seed (mixture of *Ipomoea hederacea* and *J. lacunosa* seed) will be uniformly distributed and slightly pressed onto the soil surface of each pot. The seeds will be covered with approx. 5 mm layer of moist fine siliceous sand. The number of emerging morning glory plants will be determined every 5-7 days for one month. Previous studies have shown that the number of emerging plants is inversely related to the level of damping off and seedling disease (unpublished data). Experiments on herbicidal activity will be performed using a sandy loam soil from a field, characterized as not having a significant nematode or fungal disease problem. The soil will be apportioned in 1 kg amounts and placed in 6 L polyethylene bags ("chicken bags"). Soil in each bag will be thoroughly mixed with a weed seed mixture. The mixture consists of 5 yellow nutsedge rhizomes and the seed of (number per bag): annual morning glory mix, i.e., *Ipomoea hederacea/I lacunosa*, (40); large crabgrass, i.e., *Digitaria sanguinalis*, (300); sicklepod, i.e., *Senna obtusifolia*, (60); jimsonweed, i.e., *Datura stramonium*, (80); yellow foxtail, i.e., *Setaria glauca*, (100); and redroot pigweed, i.e., *Amaranthus retroflexus*, (1000). The soil with weeds will be transferred to pots and treated as described for the experiments with nematodes and fungi. The number and species of emerging weeds will be recorded at weekly intervals for 6 wks after removal of the plastic bags.

There will be 14 treatments in each experiment arranged in a randomized complete block design with 7 replications (experimental unit=1 pot) per treatment for a total of 98 pots. It is envisioned that there will be a minimum of 6 experiments within this objective.

Objective 2. The ideal C/N ratios for glycerin acrolein mixtures to assure complete decomposition of the mixtures in soil without phytotoxic effects to succeeding crop plants will be determined. Glycerin and acrolein contain no nitrogen, so their decomposition in soil will be limited by the amount of available N in soil. The treatments may result not only in partial decomposition of glycerin-acrolein added but also in a deficiency of available N and "yellowing" of crop plants. Greenhouse experiments will be conducted. to determine the optimal amount of N needed to optimize microbial decomposition of glycerin-acrolein mixtures established from Objective I while still retaining pesticidal activity. Factorial experiments will be set up with treatments consisting of mixtures of an organic N source (e.g., urea, casein) and glycerin-acrolein solutions with the highest pesticidal activities as determined from Objective 1. The tested nitrogen sources will include urea and casein, which are both relatively inexpensive, commercially available, and exhibit considerable solubility in glycerin (Merck Index, 1989). The experiments will be set up as described for Objective 1 to determine pesticidal activities (including nematocidal, fungicidal, and herbicidal activities) of the glycerin acrolein-urea (GAU) and the glycerin-urea-casein (GUC) compositions.

Objective 3. Develop formulations suitable for field use and determine their performance for nematode control and yield response in microplot experiments with tomato and other common horticultural crops. Liquid formulations of GAU and GUC suitable for application through irrigation water will be developed based on results obtained from Objective 2. The formulations will be tested in microplot experiments at the Microplot Experimental Unit on the Auburn University campus. A microplot consists of an 1 ft$^2$ area delimited by a 2 ft-long square terra cotta chimney flue embedded in soil with 4 inches set above ground. The microplots are filled with silt-loam soil known to be infested with a variety of plant pathogenic nematodes (including *Meloidogyne incognita, Hoplolaimus galeatus, Paratrichodorus minor*, and others), and fungi (including, *R. solani* and species of *Pythium* and *Fusarium*). Microplots are fitted with a drip irrigation system in which each plot has a dripper delivering 2 gallons of water per hour.

Microplots will be treated by drenching in 1 inch-acre of water with the appropriate glycerin formulations. Immediately after application of the treatments, the plots will be covered with clear polyethylene (2 mil) mulch. After 3 wks, the mulch will be removed and soil samples for nematological analyses will be collected. Each plot will then be planted with seedlings (2/plot). There will be a minimum of 3 experiments, one with cherry tomatoes and the other two with eggplant and green pepper. The plants will be irrigated and maintained in good growing conditions following standard recommendations for production of the crops. Each microplot experiment will have 8 treatments with 8 replications arranged in a randomized complete block design. There will be thus 64 plots per experiment and crop.

Data will be collected on plant survival, phytotoxicity, growth parameters and yield. Soil and root samples will be collected at termination of the experiments to determine nematode populations and to estimate damage from fungal pathogens. Yield data will be used in preliminary economic analyses.

Example 5

Treated Crude Glycerin Combined with Organic Nitrogen

Figure 11:
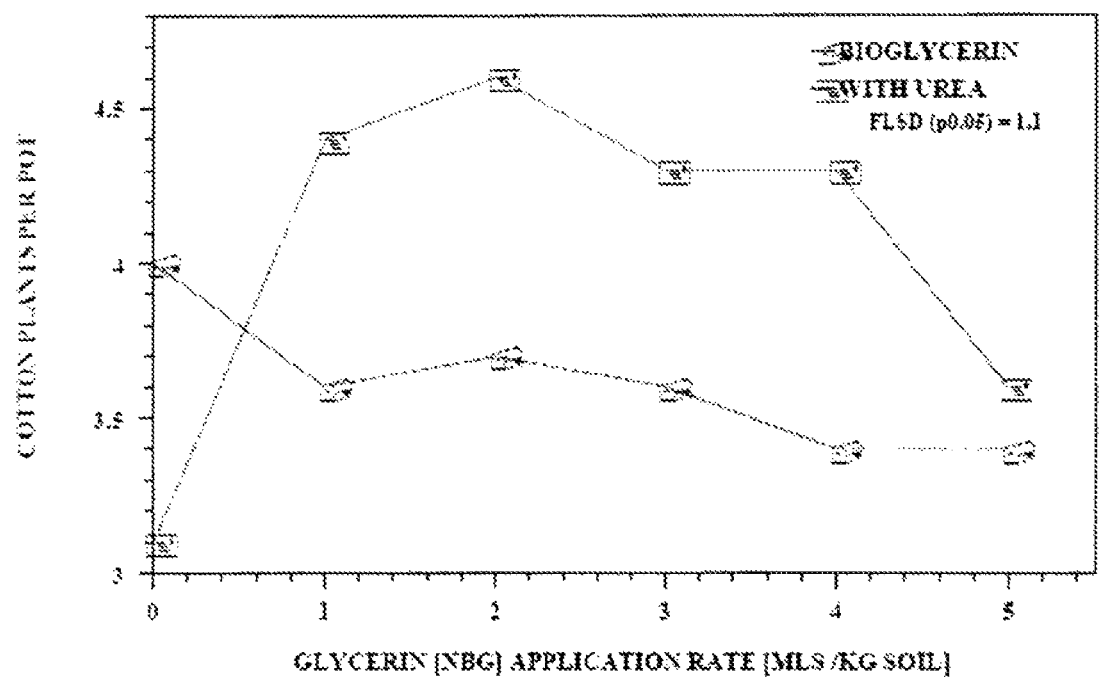
FIG. 11. The effect of a neutralized bioglycerin composition (see Example 1) at various application rates (0 ml/kg soil, 1 ml/kg soil, 2 ml/kg soil, 3 ml/kg soil, 4 ml/kg soil, or 5 ml/kg soil) with or without added urea (150 mg/kg soil) on cotton plant emergence (cotton plant per pot) was assessed. The presence of urea was observed to result in an increase in the number of cotton plants per pot.
Figure 12:
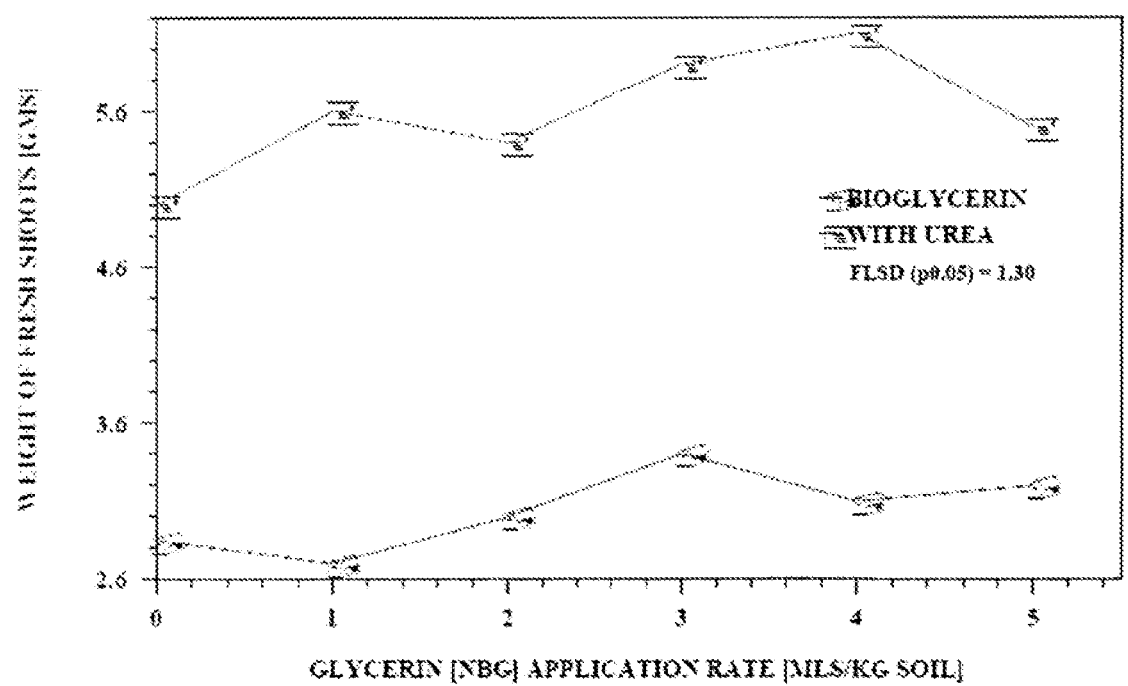
FIG. 12. The effect of a neutralized bioglycerin composition (see Example 1) at various application rates (0 ml/kg soil, 1 ml/kg soil, 2 ml/kg soil, 3 ml/kg soil, 4 ml/kg soil, or 5 ml/kg soil) with or without added urea (150 mg/kg soil) on cotton plant shoot weight (grams) was assessed. The presence of urea was observed to result in an increase in the weight of fresh shoots.

The effect of neutralized bioglycerin (NBG), either in the presence or absence of organic nitrogen, was tested on the growth of cotton plants and parasitic nematodes. Neutralized bioglycerin (NBG) was applied at rates of 0, 1, 2, 3, 4, and 5 mls/kg soil either with or without urea (150 mgs/Kg soil of the compound to achieve about 70 mgs N/Kg soil). Applications were performed by drenching the soil in aqueous solution so that the final application volume per pot was 100 mls (which is equivalent to an acre inch of irrigation). Each pot contained 1 Kg of soil infested with the reniform nematode *Rotylenchulus reniformis* and there were 7 replications (pots)/treatment. Thus, for example, for the 1 ml NBG application there were 14 pots, 7 of which received each water up to 100 mls containing 1 ml NBG; the other 7 pots received each 1 ml NBG+150 mgs urea mixed in a final volume of 100 mls. The carbon:nitrogen ratios (C/N) of the combined treatments ranged from about 5.6 for the 1 ml NBG treatment to 28 for the 5 mls NBG treatment. Urea alone (0 mls NBG) suppressed reniform nematode numbers but proved phytotoxic to cotton plants where a lower number of cotton plants per pot were observed. Applications of NBG without urea, while detrimental to the nematode (see FIG. 10), did not improve cotton plant survival and in fact was somewhat detrimental to the plants (see FIGS. 11 & 12). FIGS. 11 & 12 suggest that C:N ratios in the range of about $5.6 \leq C/N \leq 22.4$ (i.e., $1 \leq NBG \leq 4$ mls/Kg soil) are optimal for nematode control and survival of cotton plants (preferably in the range of about $11.2 \leq C/N \leq 16.8$ (i.e., $2 \leq NBG \leq 3$ mls/Kg soil)).

Urea is soluble in NBG up to 40% by weight so that the two materials can be formulated together. Ideally, the pH should be adjusted between about 4.0 and about 5.5. Buffers composed of K salts of $H_3PO_4$ and propionic acid (or other organic acids) may be particularly suitable because they form strong buffers for the required pH range and contain the nutrients P and K. Other N compounds that can be utilized in lieu of urea include, but are not limited to, guanidines, dicyandiamide, and oxamide. After adding water to the NBG (e.g., about 10-20%) standard nitrates (K or $NH_4^+$) or even ammonium sulfate and the like can be utilized for preparing fertilizer mixtures having pesticidal properties. Alternatively, the nitrate or ammonium salts may be added to the NBG as aqueous solutions.

Example 6

Use of Untreated Crude Biodiesel Glycerin for Controlling or Eliminating Weeds

The efficacy of untreated crude biodiesel glycerin for controlling or eliminating weeds was tested against crab grass, sickle pod, and morning glory. The untreated bioglycerin was applied to soil at rates of 5 mls/kg soil, 10 mls/kg soil, 11 mls/kg soil, 12 mls/kg soil, 13 mls/kg soil, 14 mls/kg soil, 15 mls/kg soil, 16 mls/kg soil, 17 mls/kg soil, 18 mls/kg soil, 19 mls/kg soil, and 20 mls/kg soil. After 5, 11, 19, or 39 days, the soil was mixed with weed seed and emerging seeds were periodically counted. Application rates of untreated bioglycerin as low as 10 mls/kg soil were found to be effective for reducing emerging weeds. Thus, untreated crude biodiesel glycerin may be utilized as such as a soil-amendment for controlling or eliminating weeds, or optionally, further may be treated as disclosed herein (e.g., neutralized, heated, refluxed, condensed, distilled, and combined with additional pesticidal or fertilizing agents).

All publications and patent applications cited in this specification are herein incorporated by reference as if each individual publication or patent application were specifically and individually indicated to be incorporated by reference.

We claim:

1. A composition comprising:
   (a) a treated glycerin composition, wherein the treated glycerin composition is treated by adding a carboxylic acid to a glycerin composition comprising glycerin obtained from vegetable or animal oils or fats, and wherein the treated glycerin composition is further treated by adding a phosphorus-containing acid; and
   (b) a glycerin-soluble nitrogen source.

2. The composition of claim 1, wherein the carboxylic acid is selected from a group consisting of acetic acid, propionic acid, butyric acid, valeric acid, citric acid or a mixture thereof.

3. The composition of claim 1, wherein the treated glycerin composition has a pH of about 4.0-8.0.

4. The composition of claim 1, wherein the nitrogen source comprises urea.

5. The composition of claim 1, wherein the phosphorus-containing acid is phosphoric acid or phosphorous acid.

6. The composition of claim 1, further comprising assimilable potassium.

7. A method for controlling soil-bourn pests in soil comprising applying the soil-amendment composition of claim 1 to the soil.

8. The method of claim 7, comprising applying the composition at an application rate of at least about 1 ml/kg soil.

9. The method of claim 7, wherein the soil-bourn pests are nematodes and the method reduces the population of nematodes in the soil by at least 50%.

10. The method of claim 9, wherein the nematodes comprise *Rotylenchulus reniformis*.

11. The method of claim 9, wherein the nematodes belong to the order Dorylaimida.

12. The method of claim 7, wherein the soil comprises beneficial microbivorous nematodes and the method does not reduce the population of the beneficial microbivorious nematodes by more than about 50%.

13. A method for controlling weeds in soil comprising applying the soil-amendment composition of claim 1 to the soil.

14. The method of claim 13, comprising applying the composition at an application rate of at least about 5 ml/kg soil.

15. The method of claim 13, wherein the weeds are selected from the group consisting of crab grass, sickle pod, and morning glory and mixtures thereof.

16. A composition comprising:
(a) a treated crude glycerin composition, wherein the treated crude glycerin composition is treated by adding a carboxylic acid to a crude glycerin composition, and wherein the treated crude glycerin composition is further treated by adding a phosphorus-containing acid; and
(b) a glycerin-soluble nitrogen source.

17. A method for controlling soil-bourn pests in soil comprising applying the soil-amendment composition of claim 16 to the soil.

18. The method of claim 17, comprising applying the composition at an application rate of at least about 1 ml/kg soil.

19. A method for controlling weeds in soil comprising applying the soil-amendment composition of claim 16 to the soil.

20. The method of claim 16, comprising applying the composition at an application rate of at least about 5 ml/kg soil.

* * * * *